United States Patent [19]

Fukumi et al.

[11] Patent Number: 5,407,933
[45] Date of Patent: Apr. 18, 1995

[54] NITROGEN-CONTAINING TETRACYCLIC COMPOUNDS HAVING ANTI-ALLERGIC AND ANTI-ASTHMATIC ACTIVITIES AND THEIR USE

[75] Inventors: Hiroshi Fukumi; Toshiaki Sakamoto; Mitsuo Sugiyama; Yoshio Iizuka; Takeshi Yamaguchi, all of Tokyo, Japan

[73] Assignee: Sankyo Company, Limited, Tokyo, Japan

[21] Appl. No.: 291,347

[22] Filed: Aug. 16, 1994

Related U.S. Application Data

[63] Continuation of Ser. No. 964,359, Oct. 21, 1992, abandoned.

[30] Foreign Application Priority Data

Oct. 23, 1991 [JP] Japan .................. 3-275125

[51] Int. Cl.[6] .................. A61K 31/55; C07D 487/14
[52] U.S. Cl. .................. 514/219; 540/555; 540/579
[58] Field of Search .................. 540/555; 514/219

[56] References Cited

U.S. PATENT DOCUMENTS

| | | | |
|---|---|---|---|
| 4,025,513 | 5/1977 | Olivie | 544/246 |
| 4,062,848 | 12/1977 | van der Burg | 544/333 |
| 4,217,452 | 8/1980 | Olivie | 544/246 |
| 4,316,900 | 2/1982 | Wasley | 540/555 |
| 4,908,365 | 3/1990 | Buzas et al. | 514/252 |
| 4,929,618 | 5/1990 | Koda et al. | 514/253 |
| 4,983,614 | 1/1991 | Buzas et al. | 514/317 |

FOREIGN PATENT DOCUMENTS

| | | |
|---|---|---|
| 0001585 | 5/1979 | European Pat. Off. |
| 0254627 | 1/1988 | European Pat. Off. |
| 0259227 | 3/1988 | European Pat. Off. |
| 0335586 | 10/1989 | European Pat. Off. |
| 0421823 | 4/1991 | European Pat. Off. |
| 0447857 | 9/1991 | European Pat. Off. |
| WO88/07997 | 10/1988 | WIPO |

*Primary Examiner*—Mukund J. Shah
*Assistant Examiner*—Philip I. Datlow
*Attorney, Agent, or Firm*—Frishauf, Holtz, Goodman & Woodward

[57] ABSTRACT

Compounds of formula (I):

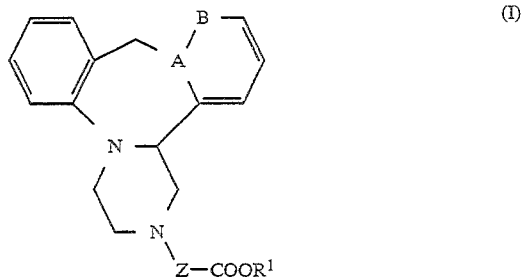

[wherein: A—B is =C=CH— or a nitrogen atom; $R^1$ is hydrogen, alkyl, aryl or aralkyl; and Z is alkylene] and pharmaceutically acceptable salts thereof are useful in the treatment and prevention of allergies and asthma.

43 Claims, No Drawings

NITROGEN-CONTAINING TETRACYCLIC COMPOUNDS HAVING ANTI-ALLERGIC AND ANTI-ASTHMATIC ACTIVITIES AND THEIR USE

This application is a continuation Ser. No. 07/964,359, filed Oct. 21, 1992, now abandoned.

The present invention relates to a series of tetracyclic compounds which are useful in the treatment and prophylaxis of allergic and asthmatic conditions. The compounds are (1,2,3,4,10,14b-hexahydrodibenzo[c,f]-pyrazino[1,2-a]azepin-2-yl) alkanoic acids and (1,2,3,4,10,14b-hexahydropyrazino[1,2-a]-pyrrolo[2,1-c][1,4]benzazepin-2-yl)alkanoic acids and esters thereof. The invention also provides methods and compositions using these compounds, as well as processes for preparing them.

A number of compounds of this general type is known. For example, mianserin, which has the formula (A):

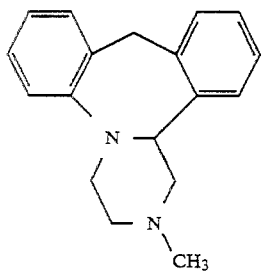

mirtazapine, which has the formula (B):

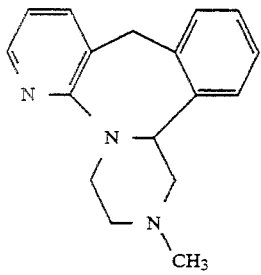

aptazapine, which has the formula (C):

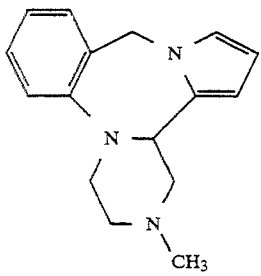

2-(2-hydroxyethyl)-1,2,3,4,10,14b-hexahydropyrazino[1,2-a]pyrrolo[2,1-c][1,4]benzodiazepine, which has the formula (D):

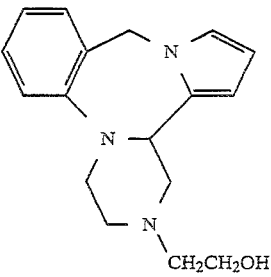

2-methoxycarbonylmethyl -1,2,3,4,10,14b-hexahydropyrazino[1,2-a]pyrrolo[2,1-c][1,4]benzodiazepine, which has the formula (E):

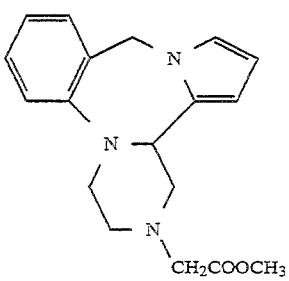

and 2-(2-carbamoylethyl)-1,2,3,4,10,14b-hexahydrodibenzo[c,f]pyrazino[1,2-a]azepine, which has the formula (F):

are disclosed in U.S. Pat. No. 4 025 513, 4,062,848, European Patent Specification No. 1585 and PCT Application No. WO-88/07997, and are said to have various activities, including anti-depressant activity and anti-histamine activity.

However, the closest prior art is believed to be European Patent Application No. 447 857, which discloses a series of tetracyclic compounds similar in structure to certain of those of the present invention. We have surprisingly discovered that those isomers of the compounds of the present invention in which the carbon atom at the 14b-position is in the R configuration are of at least equal activity and that the 14b(R) isomers are of significantly lower toxicity than the racemates described in this prior art.

The compounds referred to above which are said to possess an anti-allergic activity have been found to be not entirely satisfactory, in that the intensity of the activity is less than would be desired for a useful commercial product, and side effects, such as irritation or depression of the central nervous system, often occur. It would, therefore, be desirable to develop therapeutic agents which, whilst possessing excellent anti-histamic, anti-allergic and anti-asthmatic activities, also have no substantial adverse reactions, such as depression or irritation of the central nervous system.

In addition to this prior art, similar compounds are also disclosed in U.S. patent application Ser. No. 07/592 279, filed Oct. 3, 1990, by the present assignees, now abandoned, refiled as Ser. No. 07/962,037filed Oct. 15, 1992, and its equivalent EP Publication No. 421 823.

We have now discovered a series of tetracyclic compounds which fulfil these various desiderata.

BRIEF SUMMARY OF INVENTION

It is, therefore, an object of the invention to provide a series of new dibenzo-pyrazino-azepine and benzopyrrolo-pyrazino-azepine derivatives.

It is a further, and more specific, object of the invention to provide certain such compounds which have anti-histamic and/or anti-allergic and/or anti-asthmatic activities.

It is a still further, and more specific, object of the invention to provide certain such compounds which have excellent anti-histamic, anti-allergic and antiasthmatic activities without such adverse reactions as inducing drowsiness.

It is a further object of the invention to provide methods and compositions using these compounds.

Other objects and advantages will become apparent as the description proceeds.

The compounds of the present invention are those compounds of formula (I):

(I)

wherein:
A—B represents a group of formula =C=CH— or a nitrogen atom (=N—);
$R^1$ represents
  a hydrogen atom,
  an alkyl group having from 1 to 6 carbon atoms,
  an aryl group which has from 6 to 10 carbon atoms in an aromatic carbocyclic ring and which is unsubstituted or is substituted by at least one substituent selected from the group consisting of
    halogen atoms,
    alkyl groups having from 1 to 4 carbon atoms, and
    alkoxy groups having from 1 to 4 carbon atoms; or
  an aralkyl group in which an alkyl group having from 1 to 4 carbon atoms is substituted by at least one aryl group, as defined above; and
Z represents an alkylene group having from 3 to 7 carbon atoms;
and pharmaceutically acceptable salts thereof.

The invention also provides a pharmaceutical composition for the treatment or prophylaxis of asthma and allergies, which comprises an effective amount of an active compound in admixture with a pharmaceutically acceptable carrier or diluent, wherein the active compound is at least one compound of formula (I) or a pharmaceutically acceptable salt thereof, as defined above.

The invention still further provides a method for the treatment or prophylaxis of asthma or allergies in a mammal, which may be human, suffering from or susceptible to asthma or allergies, which method comprises administering to said mammal an effective amount of an active compound, wherein the active compound is at least one compound of formula (I) or a pharmaceutically acceptable salt thereof, as defined above.

The invention also provides processes for preparing the compounds of the present invention, which are described in more detail hereafter.

DETAILED DESCRIPTION OF INVENTION

The compounds of the present invention thus include those compounds in which A—B represents a group of formula =C=CH—, i.e. compounds of formula (Ia):

(Ia)

wherein Z and $R^1$ are as defined above, and those compounds in which A—B represents a nitrogen atom, i.e. compounds of formula (Ib):

(Ib)

wherein Z and $R^1$ are as defined above. For the avoidance of doubt, the above formulae include the peripheral numbering system employed herein.

In the compounds of formula (I), where $R^1$ represents an alkyl group having from 1 to 6 carbon atoms, this may be a straight or branched chain group having from 1 to 6 carbon atoms, and examples include the methyl, ethyl, propyl, isopropyl, butyl, isobutyl, sec-butyl, t-butyl, pentyl, isopentyl, neopentyl, t-pentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl and ethyl groups.

Where $R^1$ represents an aryl group, this is an aromatic hydrocarbon group containing from 6 to 10 carbon atoms, and preferably 6 or 10 carbon atoms. Preferred examples include the phenyl, 1-naphthyl and 2-naphthyl groups. The group may be substituted or unsubstituted, and, if substituted, has one or more of the substituents defined above. There is no particular limitation upon the number of substituents, except such as may be imposed by the number of substitutable positions (5 for the phenyl group or 7 for the naphthyl groups) and possibly by steric constraints. Examples of these substituents include:

halogen atoms such as the fluorine, chlorine, bromine and iodine atoms, preferably a fluorine, chlorine or bromine atom;

alkyl groups having from 1 to 4 carbon atoms, such as the methyl, ethyl, propyl, isopropyl, butyl, isobutyl, sec-butyl and t-butyl groups, preferably the methyl or ethyl group and more preferably the methyl group;

alkoxy groups having from 1 to 4 carbon atoms, such as the methoxy, ethoxy, propoxy, isopropoxy and butoxy groups, preferably the methoxy or ethoxy group and more preferably the methoxy group.

Of these substituents, we prefer the halogen atoms, particularly the fluorine and chlorine atoms, alkyl groups having 1 or 2 carbon atoms, particularly the methyl group, and alkoxy groups having 1 or 2 carbon atoms, particularly the methoxy group. Examples of specific substituted aryl groups include the o-, m- and p- tolyl, 2-, 3- and 4- ethylphenyl, 2-, 3- and 4-propylphenyl, 2-, 3- and 4- bromophenyl, 2-, 3- and 4-chlorophenyl, 2-, 3- and 4- fluorophenyl, 2-, 3- and 4-methoxyphenyl, 2-, 3- and 4- ethoxyphenyl, 2,4-difluorophenyl, 2,6-difluorophenyl, 2,4-dichlorophenyl, 2-chloro-4-fluorophenyl, 4-chloro-2-fluorophenyl and 6-chloro-2-fluorophenyl groups. However, the unsubstituted phenyl groups are preferred.

Where $R^1$ represents an aralkyl group, this is an alkyl group which has from 1 to 4 carbon atoms and is substituted by at least one, and preferably one or two, aryl groups, which may be as exemplified above, preferably the phenyl or naphthyl groups, which may be unsubstituted or substituted as defined and exemplified above. Examples of such aralkyl groups include the benzyl, phenethyl, diphenylmethyl (i.e. benzhydryl), triphenylmethyl (i.e. trityl), 1-phenylethyl, 3-phenylpropyl, 2-phenylpropyl, 4-phenylbutyl, (1-naphthyl)methyl, (2-naphthyl)methyl, 2-(1-naphthyl)ethyl, 1-(1-naphthyl)ethyl, 2-(2-naphthyl)ethyl, 1-(2-naphthyl)ethyl and di(1-naphthyl)methyl groups; of these, the benzyl and diphenylmethyl groups are preferred. The aryl group can be substituted or unsubstituted, as defined and exemplified above, from 1 to 3 substituents being preferred. In the case of the substituted groups, these may be any of the unsubstituted groups exemplified above, but in which the unsubstituted aryl group is replaced by one of the substituted aryl groups exemplified above. However, the unsubstituted aralkyl groups are preferred, particularly the benzyl group.

In the compounds of the present invention, Z represents an alkylene group having from 3 to 7 carbon atoms, which can be a straight or branched chain alkylene group. If the same carbon atom of the alkylene group is attached, on the one hand, to the nitrogen atom of the tetracyclic system and, on the other hand, to the group of formula —COOR$^1$, the resulting group is sometimes referred to as an alkylidene group. Examples of these alkylene groups include the trimethylene, propylene, tetramethylene, 3-methyltrimethylene [—CH$_2$CH$_2$CH(CH$_3$)—], pentamethylene, 3,3-dimethyl-trimethylene [—CH$_2$CH$_2$C(CH$_3$)$_2$—], hexamethylene, 5-menhylpentamethylene [—CH$_2$CH$_2$CH$_2$CH$_2$CH(CH$_3$)—], heptamethylene and 5,5-dimethylpentamethylene [—CH$_2$CH$_2$CH$_2$CH$_2$(CH$_3$)$_2$—] groups. Of these, we prefer the trimethylene, 3methyltrimethylene, pentamethylene, 3,3-dimethyltrimethylene, 5-methylpentamethylene, heptamethylene and 5,5-dimethylpentamethylene groups, the trimethylene and 3,3-dimethyltrimethylene groups being more preferred.

The compounds of the present invention include several basic nitrogen atoms and can, therefore, form acid addition salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction need not apply. Examples of such acid addition salts include: salts with a mineral acid, especially a hydrohalic acid (such as hydrochloric acid, hydrofluoric acid, hydrobromic acid or hydroiodic acid), or another mineral acid (such as sulfuric acid, nitric acid, carbonic acid, perchloric acid or phosphoric acid); salts with an organic carboxylic acid, such as fumaric acid, tartaric acid, oxalic acid, maleic acid, succinic acid or citric acid; salts with a sulfonic acid, e.g. an alkanesulfonic or haloalkanesulfonic acid, such as methanesulfonic acid, trifluoromethanesulfonic acid or ethanesulfonic acid, or with an arylsulfonic acid, such as benzenesulfonic acid or p-toluenesulfonic acid; and acid addition salts with an amino-acid, such as glutamic acid or aspartic acid. The fumarates and hydrochlorides are preferred.

Where $R^1$ represents a hydrogen atom, and the compound of formula (I) is therefore a carboxylic acid, this can also form salts with cations. Examples of such salts include: salts with an alkali metal, such as sodium, potassium or lithium; salts with an alkaline earth metal, such as barium or calcium; and salts with another metal, such as magnesium or aluminum.

The compounds of the present invention necessarily contain several asymmetric carbon atoms in their molecules, each of which can exist in the R-configuration or the S-configuration, and can thus form stereoisomers. Although these are all represented herein by a single molecular formula, the present invention includes both the individual, isolated isomers and mixtures, including racemates, thereof. Where stereospecific synthesis techniques are employed, individual isomers may be prepared directly; on the other hand, if a mixture of isomers is prepared, the individual isomers may be obtained by conventional resolution techniques. Preferred compounds include those in which, when A—B represents a group of formula =C=CH—, the carbon atom at the 14b-position is in the R-configuration (which demonstrate a lower toxicity than, accompanied by at least equivalent activity to, the prior art racemates of these or similar compounds), and those in which, when A—B represents a group of formula =N—, the carbon atom at the 14b-position is in the R-configuration.

In the compounds of the present invention, A-B can represent a group of formula =C=CH— or a nitrogen atom, i.e. a group of formula =N—, of which the nitrogen atom is preferred. In the case of those compounds where A-B represents a nitrogen atom, a preferred class of compounds of the present invention comprises those compounds in which $R^1$ represents a hydrogen atom, an alkyl group having from 1 to 6 carbon atoms, an unsubstituted phenyl group or an unsubstituted benzyl group, preferably a hydrogen atom or an alkyl group having from 1 to 4 carbon atoms, more preferably a hydrogen atom, a methyl group or an ethyl group, still more preferably a hydrogen atom or an ethyl group, and most preferably a hydrogen atom. Amongst these compounds of the present invention where A—B represents a nitrogen atom, we especially prefer those in which Z represents an alkylene group having 3, 5 or 7 carbon atoms, more preferably a trimethylene group or a 3,3-dimethyltrimethylene group, and most preferably a trimethylene group.

Where A—B represents a group of formula =C=CH—, a preferred class of compounds of the present invention comprises those compounds in which $R^1$ represents a hydrogen atom or an alkyl group having from 1 to 4 carbon atoms, more preferably a hydrogen atom, a methyl group or an ethyl group, still more preferably a hydrogen atom or an ethyl group, and most preferably a hydrogen atom. Amongst these compounds of the present invention where A—B represents a group of formula =C=CH—, we especially prefer those in which Z represents an alkylene group having 3,5 or 7 carbon atoms, more preferably a trimethylene group or a 3,3-dimethyltrimethylene group, and most preferably a trimethylene group.

In particular, preferred compounds of the present invention are those compounds of formula (I) in which:
A—B represents a nitrogen atom;
$R^1$ represents a hydrogen atom, an alkyl group having from 1 to 6 carbon atoms, an unsubstituted phenyl group or an unsubstituted benzyl group; and
Z represents an alkylene group having 3, 5 or 7 carbon atoms;
and, still more preferably, the carbon atom at the 14b-position is in the R-configuration.

An alternative preferred class of compounds of the present invention are those compounds of formula (I) in which:
A—B represents a group of formula =C=CH—;
$R^1$ represents a hydrogen atom or an alkyl group having from 1 to 4 carbon atoms; and
Z represents an alkylene group having 3, 5 or 7 carbon atoms;
and, still more preferably, the carbon atom at the 14b-position is in the R-configuration.

A more preferred class of compounds of the present invention are those compounds of formula (I) in which:
A—B represents a nitrogen atom;
$R^1$ represents a hydrogen atom or an alkyl group having from 1 to 4 carbon atoms; and
Z represents a trimethylene group or a 3,3-dimethyltrimethylene group;
and, still more preferably, the carbon atom at the 14b-position is in the R-configuration.

An alternative more preferred class of compounds of the present invention are those compounds of formula (I) in which:
A—B represents a group of formula =C=CH—;
$R^1$ represents a hydrogen atom, a methyl group or an ethyl group; and
Z represents a trimethylene group or a 3,3-dimethyltrimethylene group;

and, still more preferably, the carbon atom at the 14b-position is in the R-configuration.

A still more preferred class of compounds of the present invention are those compounds of formula (I) in which:
A—B represents a nitrogen atom;
$R^1$ represents a hydrogen atom, a methyl group or an ethyl group; and
Z represents a trimethylene group;
and, still more preferably, the carbon atom at the 14b-position is in the R-configuration.

An alternative still more preferred class of compounds of the present invention are those compounds of formula (I) in which:
A—B represents a group of formula =C=CH—;
$R^1$ represents a hydrogen atom or a methyl group; and
Z represents a trimethylene group;
and, still more preferably, the carbon atom at the 14b-position is in the R-configuration.

A most preferred preferred class of compounds of the present invention are those compounds of formula (I) in which:
A—B represents a nitrogen atom;
$R^1$ represents a hydrogen atom; and
Z represents a trimethylene group;
and, still more preferably, the carbon atom at the 14b-position is in the R-configuration.

An alternative most preferred class of compounds of the present invention are those compounds of formula (I) in which:
A—B represents a group of formula =C=CH—;
$R^1$ represents a hydrogen atom; and
Z represents a trimethylene group;
and, still more preferably, the carbon atom an the 14b-position is in the R-configuration.

Examples of specific compounds of the invention are those compounds of formula (Ia), in which Z and $R^1$ are as defined in Table 1, and those compounds of formula (Ib), in which Z and $R^1$ are as defined in Table 2.

In the Table, the following abbreviations are used:

| | |
|---|---|
| Bu | butyl |
| iBu | isobutyl |
| Bz | benzyl |
| Et | ethyl |
| Me | methyl |
| Ph | phenyl |
| PhEt | phenethyl |
| Pr | propyl |
| iPr | isopropyl |
| p-Tol | p-tolyl |

TABLE 1

| Cpd. No. | Z | $R^1$ |
|---|---|---|
| 1-1 | —$CH_2CH_2C(Me)_2$— | H |
| 1-2 | —$CH_2CH_2C(Me)_2$— | Me |
| 1-3 | —$CH_2CH_2C(Me)_2$— | Et |
| 1-4 | —$CH_2CH_2C(Me)_2$— | Pr |
| 1-5 | —$CH_2CH_2C(Me)_2$— | iPr |
| 1-6 | —$CH_2CH_2C(Me)_2$— | Bu |
| 1-7 | —$CH_2CH_2C(Me)_2$— | iBu |
| 1-8 | —$CH_2CH_2CH(Me)$— | H |
| 1-9 | —$CH_2CH_2CH(Me)$— | Me |
| 1-10 | —$CH_2CH_2CH(Me)$— | Et |
| 1-11 | —$CH_2CH_2CH_2CH_2C(Me)_2$— | H |
| 1-12 | —$CH_2CH_2CH_2CH_2C(Me)_2$— | Me |
| 1-13 | —$CH_2CH_2CH_2CH_2C(Me)_2$— | Et |
| 1-14 | —$CH_2CH_2C(Me)_2$— | Ph |

TABLE 1-continued

| Cpd. No. | Z | R¹ |
|---|---|---|
| 1-15 | —CH₂CH₂C(Me)₂— | Bz |
| 1-16 | —(CH₂)₃— | H |
| 1-17 | —(CH₂)₃— | Me |
| 1-18 | —(CH₂)₃— | Et |

TABLE 2

| Cpd. No. | Z | R¹ |
|---|---|---|
| 2-1 | —(CH₂)₃— | H |
| 2-2 | —(CH₂)₃— | Me |
| 2-3 | —(CH₂)₃— | Et |
| 2-4 | —(CH₂)₃— | Pr |
| 2-5 | —(CH₂)₃— | iPr |
| 2-6 | —(CH₂)₃— | Bu |
| 2-7 | —(CH₂)₃— | iBu |
| 2-8 | —(CH₂)₃— | Ph |
| 2-9 | —(CH₂)₃— | p-Tol |
| 2-10 | —(CH₂)₃— | Bz |
| 2-11 | —(CH₂)₃— | PhEt |
| 2-12 | —(CH₂)₄— | H |
| 2-13 | —(CH₂)₄— | Me |
| 2-14 | —(CH₂)₄— | Et |
| 2-15 | —(CH₂)₅— | H |
| 2-16 | —(CH₂)₅— | Me |
| 2-17 | —(CH₂)₅— | Et |
| 2-18 | —(CH₂)₅— | Pr |
| 2-19 | —(CH₂)₅— | iPr |
| 2-20 | —(CH₂)₅— | Bu |
| 2-21 | —(CH₂)₅— | Ph |
| 2-22 | —(CH₂)₅— | Bz |
| 2-23 | —(CH₂)₆— | H |
| 2-24 | —(CH₂)₆— | Me |
| 2-25 | —(CH₂)₆— | Et |
| 2-26 | —(CH₂)₇— | H |
| 2-27 | —(CH₂)₇— | Me |
| 2-28 | —(CH₂)₇— | Et |
| 2-29 | —(CH₂)₇— | Pr |
| 2-30 | —(CH₂)₇— | Bu |
| 2-31 | —(CH₂)₇— | iBu |
| 2-32 | —(CH₂)₇— | Ph |
| 2-33 | —(CH₂)₇— | Bz |
| 2-34 | —CH₂CH₂C(Me)₂— | H |
| 2-35 | —CH₂CH₂C(Me)₂— | Me |
| 2-36 | —CH₂CH₂C(Me)₂— | Et |
| 2-37 | —CH₂CH₂C(Me)₂— | Pr |
| 2-38 | —CH₂CH₂C(Me)₂— | iPr |
| 2-39 | —CH₂CH₂C(Me)₂— | Bu |
| 2-40 | —CH₂CH₂C(Me)₂— | iBu |
| 2-41 | —CH₂CH₂CH(Me)— | H |
| 2-42 | —CH₂CH₂CH(Me)— | Me |
| 2-43 | —CH₂CH₂CH(Me)— | Et |
| 2-44 | —CH₂CH₂CH₂CH₂C(Me)₂— | H |
| 2-45 | —CH₂CH₂CH₂CH₂C(Me)₂— | Me |
| 2-46 | —CH₂CH₂CH₂CH₂C(Me)₂— | Et |
| 2-47 | —CH₂CH₂C(Me)₂— | Ph |
| 2-48 | —CH₂CH₂C(Me)₂— | Bz |

Of the above compounds, the preferred compounds are Compounds No. 1-1, 1-2, 1-16, 1-17, 1-18, 2-1, 2-2, 2-3, 2-4, 2-5, 2-12, 2-15, 2-17, 2-23, 2-26, 2-34, 2-35 and 2-36, and the most preferred compounds are Compounds No.:

1-16. 4-(1,2,3,4,10,14b-Hexahydrodibenzo[c,f]pyrazino[1,2-a]azepin-2-yl) butyric acid [especially the 14b(R) isomer; and 2-1. 4-(1,2,3,4,10,14b-Hexahydropyrazino[1,2-a]pyrrolo[2,1-c][1,4]benzazepin-2-yl)butyric acid [14b(R) and 14b (S) isomers, preferably the 14b(R) isomer].

The compounds of the present invention can be prepared by a variety of methods, some of which may be well known in the art for the preparation of compounds of this type. For example, in general terms, the compounds may be prepared by reacting a compound of formula (II):

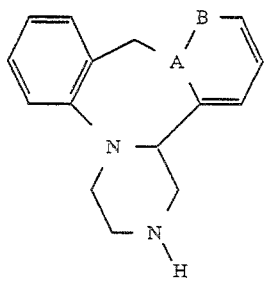

(wherein A—B is as defined above) with a halocarboxylic acid or ester thereof of formula (III):

(wherein Z and R¹ are as defined above and X represents a halogen atom, preferably a chlorine, bromine or iodine atom).

The reaction is normally and preferably carried in the presence of a base. There is no particular limitation upon the nature of the base used, and any base commonly used in reactions of this type to remove acids may equally be used here. Examples of such bases include: organic amines, such as triethylamine, N-methylmorpholine, pyridine, 4-(N,N-dimethylamino)pyridine, N,N-dimethylaniline and 1,8-diazabicyclo[5.4.0]undec-7-ene (DBU); and inorganic bases, including alkali metal carbonates, such as sodium carbonate or potassium carbonate, alkali metal hydrogencarbonates, such as sodium hydrogencarbonate or potassium hydrogencarbonate, alkali metal hydroxides, such as sodium hydroxide or potassium hydroxide, and alkaline earth metal hydroxides, such as barium hydroxide. Of these, we prefer the alkali metal carbonates, the alkali metal hydrogencarbonates and the alkali metal hydroxides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol or propanol; ketones, such as acetone, 2-butanone or 4-methyl-2-pentanone; and amides, especially fatty acid amides, such as dimethylformamide or dimethylacetamide. Of these, we prefer the ketones and dimethylformamide.

The reaction can take place over a wide range of temperatures, and the precise reaction temperature is not critical to the invention. In general, we find it convenient to carry out the reaction at a temperature of from 0° C. to 150° C., more preferably from 60° C. to 140° C. The time required for the reaction may also vary widely, depending on many factors, notably the reaction temperature and the nature of the reagents and solvent employed. However, provided that the reaction is effected under the preferred conditions outlined above, a period of from 3 to 20 hours will usually suffice.

The reaction can also be carried out in the additional presence of a small amount of an alkali metal iodide, such as sodium iodide or potassium iodide, as a catalyst.

The compounds of formula (II), which are amongst the starting materials used in this reaction, are well known or can be prepared using methods which are well known for the preparation of similar compounds. Examples of well known methods include the methods described by C. N. Filer et al. [J. Org. Chem., 46, 3344 (1981)], C. A. A. van Boeckel et al. [Rec. Trav. Chim. Pays-Bas, 104, 259 (1985)] and A. Org-Lee et. al. [J. Heterocyclic Chem., 20, 1565 (1983)].

The desired compound obtained as described above can be recovered from the reaction mixture by means of conventional recovery techniques. An example of one such technique comprises: distilling off the solvent from the reaction mixture; or, if necessary, after distilling off the solvent from the reaction mixture, pouring the concentrate into water; extracting the resulting product with a water-immiscible organic solvent; and finally distilling off the solvent from the extract. If necessary, the product can be further purified by such conventional means as recrystallization, reprecipitation or the various chromatography techniques, notably column chromatography or preparative thin layer chromatography.

In carrying out the above reaction, it is often preferred to use a compound of formula (III) in which R represents a group other than a hydrogen atom, i.e. an ester of formula (IIIa):

$$X\text{—}Z\text{—}COOR^{1a} \qquad \text{(IIIa)}$$

in which X and Z are as defined above and $R^{1a}$ represents any of the alkyl, aryl or aralkyl groups defined and exemplified above for $R^1$. This will produce a compound of formula (I) in which $R^1$ is replaced by $R^{1a}$. In this case, a compound of formula (I) in which the group represented by $R^1$ is a hydrogen atom can be prepared by hydrolysis of the corresponding compound of formula (I) in which the group represented by $R^1$ is an alkyl, aryl or aralkyl group. The hydrolysis can be carried out by conventional means, for example, by reacting the corresponding ester derivative with a base in an inert solvent.

Examples of bases which may be used include: alkali metal carbonates, such as sodium carbonate or potassium carbonate; and alkali metal or alkaline earth metal hydroxides, such as lithium hydroxide, sodium hydroxide, potassium hydroxide or barium hydroxide. Of these, we prefer the alkali metal hydroxides, such as sodium hydroxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol or propanol; ketones, such as acetone, 2-butanone or 4-methyl-2-pentanone; and ethers, such as dioxane or tetrahydrofuran. Of these, we prefer the alcohols.

The reaction can take place over a wide range of temperatures, and the precise reaction temperature is not critical to the invention. In general, we find it convenient to carry out the reaction at a temperature of from 0° C. to 120° C., more preferably from 0° C. to 80° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

The desired product obtained as described above can be recovered from the reaction mixture by means of conventional techniques. An example of one such technique comprises: distilling off the solvent from the reaction mixture; or, if necessary, after distilling off the solvent from the reaction mixture, pouring the concentrate into water; acidifying the aqueous layer or extracting the acidified aqueous layer with a water-immiscible organic solvent; and finally distilling off the solvent from the extract. If necessary, the product can be further purified by such conventional means as recrystallization, reprecipitation or the various chromatography techniques, notably column chromatography or preparative thin layer chromatography.

Optically active compounds of formula (II), which may be used to prepare optically active compounds of formula (I), can be prepared by conventional means, for example using the following methods:

One method involves acylating the compound of formula (II), optically resolving the acylated compound, and subsequently hydrolyzing or reducing the acylated compound, in order to deacylate it.

The acylation can be carried out by reacting a racemic mixture of the compound of formula (II) with an acylating agent, if necessary, in an inert solvent and optionally in the presence of a base.

Examples of acylating agents which may be used in this reaction include: (+)- or (−)-α-methoxy-α-(trifluoromethyl)phenylacetic acid, (+)- or (−)-α-methoxy-α-methylphenylacetic acid, (+)- or (−)-phenylethanesulfonic acid, (+)- or (−)-cis-2-benzamidocyclohexanecarboxylic acid and (+)- or (−)-2,2′-(1,1′-binaphthyl)phosphoric acid; acid chlorides of these acids; and (+)-or (−)-trans-1,2-cyclohexanedicarboxylic anhydride. Of these, we prefer (+)- or (−)-α-methoxy-α-(trifluoromethyl)phenylacetyl chloride and (+)- or (−)-α-methoxy-α-methylphenylacetyl chloride.

Examples of bases which may be used include the same bases as exemplified above for use in the reaction of the compound of formula (II) with the compound of formula (III), and, of these, we prefer the organic amines.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as methylene chloride or chloroform; esters, such as ethyl acetate or propyl acetate; ethers, such as diethyl ether, tetrahydrofuran or dioxane; amides, such as dimethylformamide, dimethylacetamide or hexamethylphosphoric triamide; and sulfoxides, such as dimethyl sulfoxide. Of these, we prefer the halogenated hydrocarbons, particularly methylene chloride.

The reaction can take place over a wide range of temperatures, and the precise reaction temperature is not critical to the invention. In general, we find it convenient to carry out the reaction at a temperature of from 0° C. to 100° C., more preferably from 0° C. to 40° C. The time required for the reaction may also vary widely, depending on many factors, notably the reaction temperature and the nature of the reagents and solvent employed. However, provided that the reaction is effected under the preferred conditions outlined above, a period of from 5 minutes to 20 hours (more preferably from 10 minutes to 3 hours) will usually suffice.

Resolution of the optical isomers of the acylated compounds of formula (II) can be performed by such conventional means as recrystallization, reprecipitation or the various chromatography techniques, notably column chromatography or preparative thin layer chromatography.

Deacylation of the optically active acylated compounds of formula (II) can then be accomplished by hydrolysis or reduction.

Hydrolysis can be performed in a similar manner to the hydrolysis described above for converting a compound of formula (I) in which $R^1$ represents an alkyl, aryl or aralkyl group to the corresponding compound in which $R^1$ represents a hydrogen atom.

Reduction can be carried out by contacting the acylated compound with a reducing agent in an inert solvent. Examples of reducing agents which may be used include aluminum hydride compounds, such as lithium aluminum hydride, diisobutylaluminum hydride and lithium tri-t-butoxyaluminohydride, of which we prefer diisobutylaluminum hydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, cyclohexane, benzene, toluene or xylene; and ethers, such as diethyl ether, tetrahydrofuran or dioxane, of which we prefer the hydrocarbons.

The reaction can take place over a wide range of temperatures, and the precise reaction temperature is not critical to the invention. In general, we find it convenient to carry out the reaction at a temperature of from $-110°$ C. to $-30°$ C., more preferably from $-78°$ to $-50°$ C. The time required for the reaction may also vary widely, depending on many factors, notably the reaction temperature and the nature of the reagents and solvent employed. However, provided that the reaction is effected under the preferred conditions outlined above, a period of from 30 minutes to 10 hours, more preferably from 1 to 5 hours, will usually suffice.

The desired compound obtained as described above can be recovered from the reaction mixture by conventional means, for example, by distilling off the solvent from the reaction mixture; or if necessary, after distilling off the solvent from the reaction mixture, pouring the concentrate into water, extracting it with a water-immiscible organic solvent and finally distilling off the solvent from the extract. If necessary, the product can further purified by such conventional means as recrystallization, reprecipitation or the various chromatography techniques, notably column chromatography or preparative thin layer chromatography.

Another method of preparing an optically active isomer of the compound of formula (II) consists of optical resolution of a racemic mixture of the isomers of the compound of formula (A) or (C), followed by demethylation.

A racemic mixture of the isomers of the compound of formula (A) or (C) may be optically resolved by treating the racemic mixture with an optically active carboxylic acid in an inert solvent to produce salts of the diastereoisomers, separating the salts and then treating them with a base.

Examples of optically active carboxylic acids which may be used for preparing a diastereoisomeric salt include: (+)-tartaric acid, (−)-dibenzoyltartaric acid, (−)-ditoluoyltartaric acid, (−)-diacetyltartaric acid, (−)-malic acid, (+)-10-camphorsulfonic acid, (+)-camphoric acid, (−)-pyroglutamic acid, (+)-aspartic acid, (+)-phenylethanesulfonic acid, (+)-mandelic acid, (+)-cis-2-benzamidocyclohexanecarboxylic acid, and (+)-2,2′-(1,1′-binaphthyl)phosphoric acid and optical isomers thereof. Of these, we prefer (−)-dibenzoyltartaric acid, (−)-ditoluoyltartaric acid, (−)-diacetyltartaric acid or (−)-malic acid and optical isomers thereof.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; alcohols, such as methanol, ethanol, propanol or isopropanol; ethers, such as tetrahydrofuran or dioxane; ketones, such as acetone, methyl ethyl ketone or 4-methyl-2-pentanone; and amides, such as dimethylformamide or dimethylacetamide. A single one of these solvents may be used or a mixture of two or more may be used. Of these solvents, we prefer the alcohols.

Treatment of a racemic mixture of the compound of formula (A) or (C) with an optically active acid can normally be carried out at about room temperature, and normally the reaction will be sufficiently complete in a period of from 10 minutes to 2 hours.

Separation of the diastereoisomeric salts can be conducted by such conventional means as filtration or recrystallization.

The resulting optically active salt my be treated with a base by dissolving it in an aqueous solution of a base, such as sodium hydroxide, potassium hydroxide, sodium carbonate, potassium carbonate, sodium hydrogencarbonate or potassium hydrogencarbonate, extracting the solution with a water-immiscible solvent and then distilling off the solvent.

Demethylation of the optically active compound of formula (A) or (C) can be conducted in a similar manner to such well-known methods as that described in Rec. Tray. Chim. Pays-Bas, 104, 259 (1985).

The desired compound prepared as described above can be recovered from the reaction mixture by conventional means, for example, by distilling off the solvent from the reaction mixture; or, if necessary, after distilling off the solvent, pouring the concentrate into water, extracting it with a water-immiscible organic solvent, and finally distilling off the solvent from the extract. If necessary, the product can be further purified by conventional means, for example, recrystallization, reprecipitation or the various chromatography techniques, notably column chromatography or preparative thin layer chromatography.

The tetracyclic compounds of the present invention have, as shown in the following biological activity data, exhibited excellent anti-histamic, anti-allergic and anti-asthmatic activities. Moreover, they lack various side effects which are known to be a problem with other compounds having such activity, such as causing drowsiness, insomnia or irritability, Accordingly, the compounds are useful as therapeutic agents for the treatment or prophylaxis of allergic diseases or asthma.

The compounds of the present invention may therefore be used in the treatment of such disorders, and, for this purpose, may be formulated as conventional pharmaceutical preparations, as is well known in the art. Thus, the compounds may be administered orally, e.g. in the form of tablets, capsules, granules, powders, syrups, sprays or other such well known forms, or parenterally, e.g. by injections, sprays, eyedrops, poultices, adhesive plasters or suppositories.

These pharmaceutical preparations can be prepared by conventional means and may contain known adjuvants of a type commonly used in this field, for example vehicles, binders, disintegrators, lubricants, stabilizers, corrigents, etc. depending upon the intended use and form of the preparation. The dose will depend upon the condition, age, and body weight of the patient as well as upon the nature and severity of the disorder to be treated, but in the case of oral administration to an adult human patient, we would normally suggest a total daily dose of from 0.01 mg to 100 mg (more preferably from 0.1 mg to 50 mg), which may be administered in a single dose or in divided doses, e.g. from ode to three times a day.

The preparation of the compounds of the present invention is further illustrated by the following Examples. The biological activity of certain of the compounds of the present invention is illustrated in the following Test Examples.

EXAMPLE 1

Ethyl(R)-2,2-dimethyl-4-(1,2,3,4,10,14b-hexahydrodibenzo[c,f]pyrazino[1,2-a]azepin-2-yl) butyrate and its fumarate A mixture prepared by adding 10.51 g of (R)-1,2,3,4,10,14b-hexahydrodibenzo[c,f]pyrazino[1,2-a]azepine, 0.63 g of sodium iodide, 17.41 g of potassium carbonate and 9.0 g of ethyl 2,2-dimethyl-4-chlorobutyrate to 200 ml of dimethylformamide was stirred at 100° C. for 16 hours. At the end of this time, the mixture was cooled, and then insoluble materials were removed from the reaction mixture by filtration. The filtrate was concentrated by evaporation under reduced pressure, and the residue was extracted with toluene. The extract was freed from the solvent by distillation under reduced pressure, and the residual oil was purified by column chromatography through silica gel, using a 2:1 by volume mixture of hexane and ethyl acetate as the eluent, to give 2.76 g (yield 17%) of the title compound, as an oil.

Infrared Absorption Spectrum (CHCl$_3$), $\nu_{max}$ cm$^{-1}$: 2970, 2810, 1765, 1720, 1595.

The fumarate of the title compound was prepared by adding an equimolar amount of fumaric acid to a solution of the title compound in ethanol, and the resulting crystals, melting at 133°–138° C., were recrystallized from ethanol.

EXAMPLE 2

(R)-2.2-Dimethyl-4-(1,2,3,4.10,14b-hexahydrodibenzo[c,f]pyrazino[1,2-a]azepin-2-yl)butyric acid and its hydrochloride 3 ml of a 10% w/v aqueous solution of sodium hydroxide and 3 ml of water were added to a solution of 1.65 g of ethyl(R)-2,2-dimethyl-4-(1,2,3,4,10,14b-hexahydrodibenzo[c,f]pyrazino[1,2-a]azepin-2-yl)butyrate (prepared as described in Example 1) in 10 ml of ethanol, and the resulting mixture was heated under reflux for 20 hours. At the end of this time, the pH of the reaction mixture was adjusted to a value of 4 by the addition of 10% w/v aqueous hydrochloric acid. The mixture was then extracted with ethyl acetate, and the extract was freed from the solvent by distillation under reduced pressure, to give 0.65 g (yield 42%) of the title compound, as crystals, melting at 211°–214° C.

Infrared Absorption Spectrum (KBr), $\nu_{max}$ cm$^{-1}$: 2957, 2920, 2826, 1704, 1599.

The hydrochloride of the title compound was prepared as crystals, melting at 277°–279° C. (with decomposition), by adding a 4N solution of hydrogen chloride in ethyl acetate to a solution of the title compound in ethyl acetate, and distilling off the solvent under reduced pressure.

EXAMPLE 3

(R)-4-(1,2,3,4,10,14b-Hexahydropyrazino[1,2-a]pyrrolo[2,1-c][1,4]benzazepin-2-yl)butyric acid hydrochloride A mixture prepared by adding 1.0 g of (R)-1,2,3,4,10,14b-hexahydropyrazino[1,2-a]pyrrolo[2,1-c][1,4]benzazepine, 0.76 g of ethyl 4-chlorobutyrate, 1.05 g of sodium carbonate and 0,063 g of sodium iodide to 10 ml of dimethylformamide was stirred at 100° C. for 3 hours. At the end of this time, the reaction mixture was poured into ice-water and then extracted with toluene. The extract was freed from the solvent by distillation under reduced pressure, and the residual oil (the ethyl ester of the title compound) was dissolved in a mixture of 2.2 ml of water and 11 ml of ethanol. 2.2 ml of a 10% sodium hydroxide solution were added to this solution, and the resulting mixture was stirred at room temperature for 1 hour. The reaction mixture was then washed with 10 ml of toluene, and the pH of the aqueous layer was adjusted to a value of 2.6 by the addition of 10% w/v aqueous hydrochloric acid. The crystals which precipitated were collected by filtration, to give 0.62 g (yield 46%) of the title compound, melting at 263°–265° C. (with decomposition).

Infrared Absorption Spectrum (KBr), $\nu_{max}$ cm$^{-1}$: 2931, 2841, 2745, 1728, 1492, 1306.

$[\alpha]_D^{23} = +228.9°$ (c=0.99, 1N aqueous sodium hydroxide).

EXAMPLE 4

(S)-4-(1,2,3,4,10,14b-Hexahydropyrazino[1,2-a]pyrrolo[2,1-c][1,4]benzazepin-2-yl)butyrate acid hydrochloride A procedure similar to that described in Example 3 was repeated, except that a similar amount of (S)-1,2,3,4,10,14b-hexahydropyrazino[1,2-a]pyrrolo[2,1-c][1,4]benzazepine was used instead of the (R)-1,2,3,4,10,14b-hexahydropyrazino[1,2-a]pyrrolo[2,1-c][1,4]benzazepine, give the title compound as crystals, melting at 265°–266° C. (with decomposition), in a 42% yield.

Infrared Absorption Spectrum (KBr), $\nu_{max}$ cm$^{-1}$: 2931, 2841, 2744, 1729, 1493, 1480.

$[\alpha]_D^{23} = -225.8°$ (c=0.97, 1N aqueous sodium hydroxide).

EXAMPLE 5

Ethyl(R)-4-(1,2,3,4,10,14b-hexahydrodibenzo[c,f-]pyrazino[1,2-a]azepin-2-yl)butyrate and its fumarate A procedure similar to that described in Example 1 was repeated, except that a similar amount of ethyl 4-bromobutyrate was used in place of the ethyl 2,2-dimethyl-4-chlorobutyrate, to give the title compound as an oil, in a 99% yield.

Infrared Absorption Spectrum (CHCl$_3$), $\nu_{max}$ cm$^{-1}$: 2960, 2830, 1730, 1600, 1495.

The fumarate of the title compound was prepared by adding an equimolar amount of fumaric acid to a solution of the title compound in ethanol, stirring the resulting mixture at room temperature for 30 minutes, and then removing the solvent by distillation under reduced pressure. The resulting crystalline product was recrystallized from ethanol, to give the title compound, melting at 139°–141° C.

EXAMPLE 6

(R)-4-(1.2,3,4,10,14b-Hexahydrodibenzo[c,f-]pyrazino[1,2-a]azepin-2-yl)butyric acid hydrochloride 20 ml of a 10% w/v aqueous solution of sodium hydroxide were added to a solution of 14.34 g of ethyl (R)-4-(1,2,3,4,10,14b-hexahydrodibenzo[c,f-]pyrazino[1.2-a]azepin-2-yl)butyrate (prepared as described in Example 5) in 100 ml of ethanol, and the resulting mixture was stirred at room temperature for 1 hour. At the end of this time, the pH of the reaction mixture was adjusted to a value of 2 by the addition of 10% w/v aqueous hydrochloric acid, and the solvent was removed by distillation under reduced pressure. The crystals which precipitated were collected by filtration and dried, to give the title compound, melting at 265°–268° C. (with decomposition), in a 76% yield.

Infrared Absorption Spectrum (KBr), $\nu_{max}$ cm$^{-1}$: 3029, 2928, 2912, 2700, 2585, 1727.

$[\alpha]_D^{23} = -269.3°$ (c=0.97 methanol).

EXAMPLE 7

Ethyl(R)-5-(1,2,3,4,10,14b-hexahydropyrazino[1,2-a]pyrrolo-[2,1-c][1,4]benzazepin-2-yl)valerate A procedure similar to that described in Example 1 was repeated, except that similar amounts of ethyl (R)-1,2,3,4,10,14b-hexahydropyrazino[1,2-a]pyrrolo[2,1-c][1,4]benzazepine and ethyl 5-bromovalerate were used in place of the(R)-1,2,3,4,10,14b-hexahydrodibenzo[c,f]pyrazino[1,2-a]azepine and ethyl 2,2-dimethyl-4-chlorobutyrate, to give the title compound as an oily substance in a yield of 91%.

Infrared Absorption Spectrum (CHCl$_3$), $\nu_{max}$ cm$^{-1}$: 2980, 2930, 2810, 1725, 1600, 1495.

EXAMPLE 8

Ethyl(R)-6-(1,2,3,4,10,14b-hexahydropyrazino[1,2-a]pyrrolo[2,1-c][1,4]benzazepin-2-yl)hexanoate A procedure similar to that described in Example 1 was repeated, except that similar amounts of (R)-1,2,3,4,10,14b-hexahydropyrazino[1,2-a]pyrrolo[2,1-c][1,4]benzazepine and ethyl 6-bromohexanoate were used in place of the(R)-1,2,3,4,10,14b-hexahydrodibenzo[c,f]pyrazino[1,2-a]azepine and ethyl 2,2-dimethyl-4-chlorobutyrate, to give the title compound as an oily substance in a yield of 94%.

Infrared Absorption Spectrum (CHCl$_3$), $\nu_{max}$ cm$^{-1}$: 3000, 2940, 2810, 1725, 1600, 1495.

EXAMPLE 9

(R)-6-(1,2,3,4,10,14b-Hexahydropyrazino[1,2-a]pyrrolo[2,1-c][1,4]benzazepin-2-yl)hexanoic acid hydrochloride 2 ml of a 10% w/v aqueous solution of sodium hydroxide and 2 ml of water were added to a solution of 1.5 g of ethyl (E)-6-(1,2,3,4,10,14b-hexahydropyrazino[1,2-a]pyrrolo[2,1-c][1,4]benzazepin-2-yl)hexanoate in 2 ml of ethanol, and the mixture was stirred at room temperature for 1 hour. At the end of this time, sufficient 1N aqueous hydrochloric acid was added to adjust the pH to a value of 2.55. The crystalline substance which separated was recovered by filtration and dried, to afford the title hydrochloride as crystals, melting at 248°–249° C. ( with decomposition), in a yield of 80%.

Infrared Absorption Spectrum (KBr), $\nu_{max}$ cm$^{-1}$: 2990, 2950, 2915, 2570, 2500, 1720, 1595.

EXAMPLE 10

(R)-5-(1,2,3,4,10,14b -Hexahydropyrazino[1,2-a]pyrrolo[2,1-c][1,4]benzazepin-2-yl)valeric acid hydrochloride A procedure similar to that described in Example 9 was repeated, except that ethyl(R)-5(1,2,3,4,10,14b-hexahydropyrazino[1,2-a][1,4]benzazepin-2-yl)valerate was used, to give the title compound as crystals, melting at 220°–223° C. (with decomposition), in a yield of 75%.

Infrared Absorption Spectrum (KBr), $\nu_{max}$ cm$^{-1}$: 3100, 3065, 2940, 2570, 2500, 1735, 1720, 1600.

BIOLOGICAL ACTIVITY

The biological activity of the compounds of the present invention is illustrated by the following Test Examples.

TEST EXAMPLE 1

Inhibitory effect on passive cutaneous anaphylaxis (PCA) in rats

According to Mona's method [I. Mona, Immunology, 7, 681–699 (1964)], antiserum (256 times the PCA titer) of rat against egg albumin was prepared and diluted four times with physiological saline. Male SD rats (5 weeks old) were used as the test animals in groups, each containing 4 animals. The rats were sensitized by intradermal injection of 0.05 ml of the diluted antiserum solution in the dorsal position. 48 hours after this injection, a suspension of the test compound in an aqueous 0.5% w/v tragacanth solution was orally administered to the rats, which had been fasted for one day. 60 minutes later they were injected in the caudal vein with 5 ml/kg body weight of physiological saline containing 0.4% w/v of egg albumin and 1.0% w/v of Evans Blue. 30 minutes after this last injection, the rats were sacrificed with carbon dioxide and the Evans Blue exuded in the dorsal intradermal portion was determined according to Harada's method (Harada et al., J. Pharm. Pharmac., 23, 218–219 (1971)].

The results achieved from the test groups which were treated with a test compound were evaluated to determine the inhibitory rate by comparison with the average amount of exuded dye in a control group, which was non given the test compound.

The inhibitory rate was calculated by the following equation.

Inhibitory rate (%)=(1-B/A)×100

A: amount of exuded dye in the control group

B: amount of exuded dye in the test group.
The results are shown in Table 3.

TABLE 3

| Compound of Example No. | Dose (p.o., mg/kg) | Inhibitory rate (%) |
|---|---|---|
| 3 | 0.2 | 72 |
|   | 0.05 | 66 |
| 6 | 0.2 | 67 |
|   | 0.05 | 55 |
| Prior art compound (D) | 3.1 | 30 |
| Prior art compound (F) | 3.1 | 52 |

Prior art compounds (D) and (F) are as previously defined when discussing the prior art. From these results it can be seen that the compounds of the present invention are substantially more active than the compounds of the prior art.

TEST EXAMPLE 2

Effect on antigen-induced bronchoconstriction in sensitized guinea pigs

The test animals used were male guinea pigs of the Hartley strain (weighing about 400 to 500 g). These animals were sensitized according to Morris' method [H. R. Morris; Br. J. Pharmac., 67, 179–184 (1979)]. The guinea pigs were injected twice subcutaneously and intraperitoneally, each time with 25 mg of egg albumin (grade 5, Sigma) at weekly intervals. 7 days after the second of these weekly injections, the animals were fasted for one day and then exposed to an aerosol of egg albumin (10 mg/ml). All of the animals so exposed responded with convulsions, indicating respiratory distress due to airway constriction, within 6 minutes.

60 minutes before the egg albumin challenge, one of the test compounds shown in the following Table 4 was administered orally to each of the animals. The compound was regarded as effective if the animal did not respond with convulsions during the 6 minutes inhalation. The results are shown in Table 4.

TABLE 4

| Compound of Example No. | Dose (p.o., mg/kg) | Inhibitory rate (%) |
|---|---|---|
| 3 | 0.1 | 100 |
|   | 0.025 | 60 |
| 6 | 0.4 | 100 |
|   | 0.1 | 80 |
|   | 0.025 | 40 |

We claim:

1. A compound of formula (I):

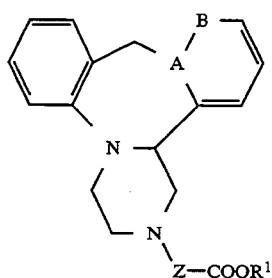

(I)

wherein:
A—B represents a nitrogen atom;
$R^1$ represents
a hydrogen atom,
an alkyl group having from 1 to 6 carbon atoms,
an aryl group which has from 6 to 10 carbon atoms in an aromatic carbocyclic ring and which is unsubstituted or is substituted by at least one substituent selected from the group consisting of halogen atoms,
alkyl groups having from 1 to 4 carbon atoms, and
alkoxy groups having from 1 to 4 carbon atoms; or
an aralkyl group in which an alkyl group having from 1 to 4 carbon atoms is substituted by at least one aryl group, as defined above; and
Z represents an alkylene group having from 3 to 7 carbon atoms;
or a pharmaceutically acceptable salt thereof.

2. The compound of claim 1, wherein the carbon atom at the 14b-position is in the R-configuration.

3. The compound of claim 1, wherein $R^1$ represents a hydrogen atom, an alkyl group having from 1 to 6 carbon atoms, an unsubstituted phenyl group or an unsubstituted benzyl group.

4. The compound of claim 1, wherein $R^1$ represents a hydrogen atom or an alkyl group having from 1 to 4 carbon atoms.

5. The compound of claim 1, wherein $R^1$ represents a hydrogen atom, a methyl group or an ethyl group.

6. The compound of claim 1, wherein $R^1$ represents a hydrogen atom or an ethyl group.

7. The compound of claim 1, wherein $R^1$ represents a hydrogen atom.

8. The compound of claim 1, wherein Z represents an alkylene group having 3,5 or 7 carbon atoms.

9. The compound of claim 1, wherein Z represents a trimethylene group or a 3,3-dimethyltrimethylene group.

10. The compound of claim 1, wherein Z represents a trimethylene group.

11. The compound of claim 1, wherein:
$R^1$ represents a hydrogen atom, an alkyl group having from 1 to 6 carbon atoms, an unsubstituted phenyl group or an unsubstituted benzyl group; and
Z represents an alkylene group having 3,5 or 7 carbon atoms.

12. The compound of claim 11, wherein the carbon atom at the 14b-position is in the R-configuration.

13. The compound of claim 1, wherein:
$R^1$ represents a hydrogen atom or an alkyl group having from 1 to 4 carbon atoms; and
Z represents a trimethylene group or a 3,3-dimethyltrimethylene group.

14. The compound of claim 13, wherein the carbon atom at the 14b-position is in the R-configuration.

15. The compound of claim 1, wherein:
$R^1$ represents a hydrogen atom, a methyl group or an ethyl group; and
Z represents a trimethylene group.

16. The compound of claim 15, wherein the carbon atom at the 14b-position is in the R-configuration.

17. The compound of claim 1, wherein:
$R^1$ represents a hydrogen atom; and
Z represents a trimethylene group.

18. The compound of claim 17, wherein the carbon atom at the 14b-position is in the R-configuration.

19. The compound of claim 1, selected from the group consisting of 4-(1,2,3,4,10,14b-hexahydropyrazino[1,2-a]pyrrolo[2,1-c][1,4]benzazepin-2-yl)butyric acid and pharmaceutically acceptable salts and esters thereof.

20. The compound of claim 1, selected from the group consisting of 14b(R)-4-(1,2,3,4,10,14b-hexahydropyrazino[1,2-a]pyrrolo[2,1-c][1,4]benzazepin-2-yl)butyric acid and pharmaceutically acceptable salts and esters thereof.

21. The compound of claim 1, selected from the group consisting of 14b(S)-4-(1,2,3,4,10,14b-hexahydropyrazino[1,2-a]pyrrolo[2,1-c][1,4]benzazepin-2-yl)butyric acid and pharmaceutically acceptable salts and esters thereof.

22. A pharmaceutical composition for the treatment or prophylaxis of asthma and allergies, which comprises an effective amount of an active compound in admixture with a pharmaceutically acceptable carrier or diluent, wherein the active compound is at least one compound of formula (I) or a pharmaceutically acceptable salt thereof, as claimed in claim 1.

23. A pharmaceutical composition for the treatment or prophylaxis of asthma and allergies, which comprises an effective amount of an active compound in admixture with a pharmaceutically acceptable carrier or diluent, wherein the active compound is at least one compound of formula (I) or a pharmaceutically acceptable salt thereof, as claimed in claim 1.

24. The composition of claim 23, wherein the carbon atom at the 14b-position is in the R-configuration.

25. The composition of claim 24, wherein:
R$^1$ represents a hydrogen atom, an alkyl group having from 1 to 6 carbon atoms, an unsubstituted phenyl group or an unsubstituted benzyl group; and
Z represents an alkylene group having 3,5 or 7 carbon atoms.

26. The composition of claim 24, wherein:
R$^1$ represents a hydrogen atom; and
Z represents a trimethylene group.

27. The composition of claim 24, wherein said active compound is selected from the group consisting of 4-(1,2,3,4,10,14b-hexahydropyrazino[1,2-a]pyrrolo[2,1-c][[1,4]benzazepin-2-yl)butyric acid and pharmaceutically acceptable salts and esters thereof.

28. The composition of claim 24, wherein said active compound is selected from the group consisting of 14b(R)-4-(1,2,3,4,10,14b-hexahydropyrazino[1,2-a]pyrrolo[2,1-c][1,4]benzazepin-2-yl)butyric acid and pharmaceutically acceptable salts and esters thereof.

29. A method for the treatment or prophylaxis of asthma or allergies in a mammal suffering from or susceptible to asthma or allergies, which method comprises administering to said mammal an effective amount of an active compound, wherein the active compound is at least one compound of formula (I) or a pharmaceutically acceptable salt thereof, as claimed in claim 1.

30. A method for the treatment or prophylaxis of asthma or allergies in a mammal suffering from or susceptible to asthma or allergies, which method comprises administering to said mammal an effective amount of an active compound, wherein the active compound is at least one compound of formula (Ib) or a pharmaceutically acceptable salt thereof, wherein formula (Ib) is defined as follows:

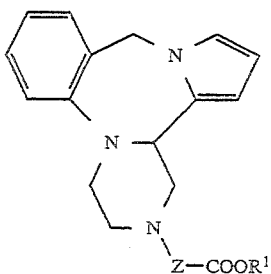

wherein:
R$^1$ represents
a hydrogen atom,
an alkyl group having from 1 to 6 carbon atoms,
an aryl group which has from 6 to 10 carbon atoms in an aromatic carbocyclic ring and which is unsubstituted or is substituted by at least one substituent selected from the group consisting of halogen atoms,
alkyl groups having from 1 to 4 carbon atoms, and
alkoxy groups having from 1 to 4 carbon atoms; or
an aralkyl group in which an alkyl group having from 1 to 4 carbon atoms is substituted by at least one aryl group, as defined above; and
Z represents an alkylene group having from 3 to 7 carbon atoms.

31. The method of claim 30, wherein the carbon atom at the 14b-position is in the R-configuration.

32. The method of claim 31, wherein:
R$^1$ represents a hydrogen atom, an alkyl group having from 1 to 6 carbon atoms, an unsubstituted phenyl group or an unsubstituted benzyl group; and
Z represents an alkylene group having 3,5 or 7 carbon atoms.

33. The method of claim 31, wherein:
R$^1$ represents a hydrogen atom; and
Z represents a trimethylene group.

34. The method of claim 30, wherein said active compound is selected from the group consisting of 4-(1,2,3,4,10,14b-hexahydropyrazino[1,2-a]pyrrolo[2,1-c][1,4]benzazepin-2-yl)butyric acid and pharmaceutically acceptable salts and esters thereof.

35. The method of claim 30, wherein said active compound is selected from the group consisting of 14b(R)-4-(1,2,3,4,10,14b-hexahydropyrazino[1,2-a]pyrrolo[2,1-c][1,4]benzazepin-2-yl)butyric acid and pharmaceutically acceptable salts and esters thereof.

36. The method of claim 30, wherein the carbon atom at the 14b-position is in the R-configuration.

37. The method of claim 30, wherein R$^1$ represents a hydrogen atom or an alkyl group having from 1 to 4 carbon atoms.

38. The method of claim 30, wherein R$^1$ represents a hydrogen atom, a methyl group or an ethyl group.

39. The method of claim 30, wherein R$^1$ represents a hydrogen atom or an ethyl group.

40. The method of claim 30, wherein R$^1$ represents a hydrogen atom.

41. The method of claim 30, wherein Z represents an alkylene group having 3, 5 or 7 carbon atoms.

42. The method of claim 30, wherein Z represents a trimethylene group or a 3,3-dimethyltrimethylene group.

43. The method of claim 30, wherein Z represents a trimethylene group.

* * * * *